US006840916B2

(12) United States Patent
Kozersky

(10) Patent No.: US 6,840,916 B2
(45) Date of Patent: Jan. 11, 2005

(54) ORTHOSIS FOR SUPPORTING SPINAL STRUCTURES

(76) Inventor: David J. Kozersky, 2627 Haverford Rd., Columbus, OH (US) 43220

( * ) Notice: Subject to any disclaimer, the term of this patent is extended or adjusted under 35 U.S.C. 154(b) by 107 days.

(21) Appl. No.: 10/353,686

(22) Filed: Jan. 29, 2003

(65) Prior Publication Data

US 2004/0147861 A1 Jul. 29, 2004

(51) Int. Cl.$^7$ .................................................. A61F 5/00
(52) U.S. Cl. ............................................. 602/19; 602/5
(58) Field of Search ............................... 602/5, 18, 19; 2/44, 45; 128/96.1, 869

(56) References Cited

U.S. PATENT DOCUMENTS

| | | | | |
|---|---|---|---|---|
| 4,245,627 A | * | 1/1981 | Mignard | 602/19 |
| 4,658,807 A | * | 4/1987 | Swain | 602/19 |
| 5,012,798 A | * | 5/1991 | Graf et al. | 602/19 |
| 5,158,531 A | * | 10/1992 | Zamosky | 602/19 |
| 5,267,948 A | * | 12/1993 | Elliott | 602/19 |
| 5,362,304 A | | 11/1994 | Varn | |
| 5,433,697 A | * | 7/1995 | Cox | 602/19 |
| 5,437,614 A | * | 8/1995 | Grim | 602/19 |
| 5,451,200 A | * | 9/1995 | LaBella et al. | 602/19 |
| 5,503,621 A | * | 4/1996 | Miller | 602/19 |
| 5,564,788 A | | 10/1996 | Warhaftig | |
| 5,718,670 A | | 2/1998 | Bremer | |
| 5,853,378 A | | 12/1998 | Modglin | |
| 5,911,697 A | * | 6/1999 | Biedermann et al. | 602/19 |
| 5,967,998 A | | 10/1999 | Modglin | |
| 6,126,660 A | | 10/2000 | Dietz | |
| 6,213,968 B1 | | 4/2001 | Heinz et al. | |

OTHER PUBLICATIONS

Boston Brace International; LS 540 Lumbo Sacral Flexion Orthosis; publication; date of publication unknown.
Atlanta International; Want Greater Compliance From Your Patients?; publication; date of publication unknown.
B&G Rehab, Inc.; Flex L.S.O. Support; publication; date of publication unknown.
Aspen Medical Products; LSO/TLSO Lumbosacral Bracing System; publication; date of publication unknown.
Boston Brace International; The Biomechanics of Spinal Bracing; magazine supplement; Jun. 2002.
Professor J. Harms, MD; SofTec Lumbo Multifunctional Support; publication; date of publication unknown.

* cited by examiner

Primary Examiner—Michael Brown
(74) Attorney, Agent, or Firm—Francis T. Kremblas, Jr.; Kremblas, Foster, Phillips & Pollick

(57) ABSTRACT

A custom-fit spinal orthosis including a pair of semi-rigid side panels configured to fit in close-fitting relationship to a wearer's torso. Each side panel includes an anterior edge disposed in overlapping releasably fixed relationship to the other side panel to enclose a major portion of the front of a wearer's torso. The posterior edges of each side panel are disposed near the spinal column of the wearer and are releasably fixed to a discrete posterior panel overlying a length of the wearer's spine. The posterior panel and the side panel are provided with cooperating vertically spaced horizontally extending slots aligned with vertically spaced openings to accept releasably fixed fasteners to connect the side panels and posterior panel together in an adjustable relationship. The posterior panel is heat-deformable for shaping into a rigid curve conforming to the wearer's lumbar curve to provide a high degree of anatomically desirable support for the wearer's spine in cooperating relationship with the side panels mounted in close-fitting relationship to the wearer's torso.

6 Claims, 9 Drawing Sheets

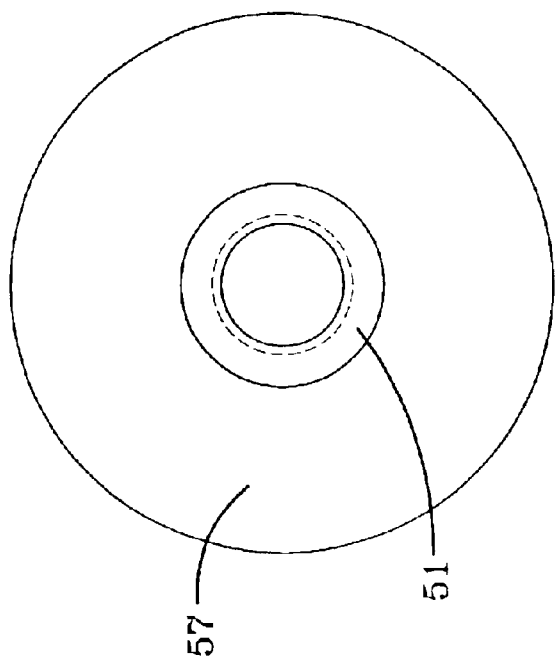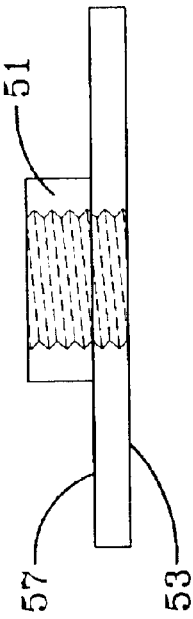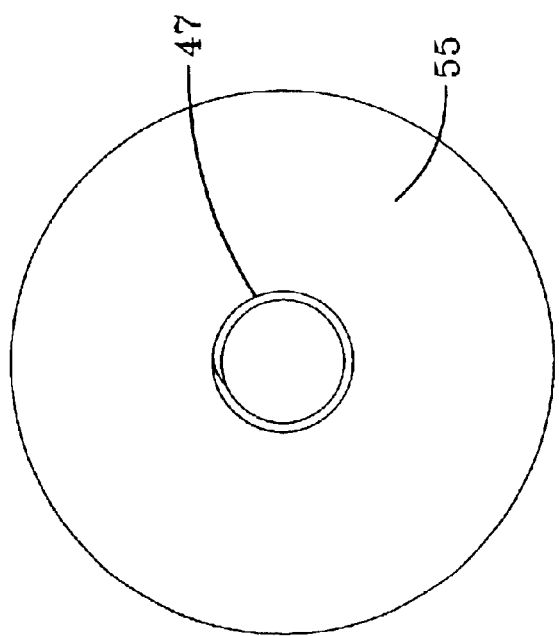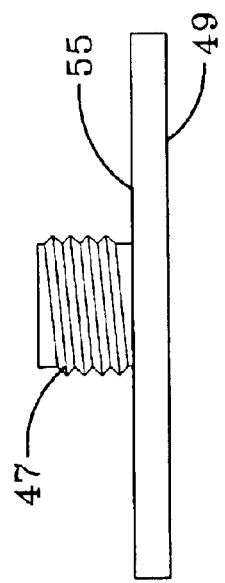

ORTHOSIS FOR SUPPORTING SPINAL STRUCTURES

CROSS-REFERENCES TO RELATED APPLICATIONS (Not Applicable)

STATEMENT REGARDING FEDERALLY-SPONSORED RESEARCH AND DEVELOPMENT (Not Applicable)

REFERENCE TO AN APPENDIX (Not Applicable)

BACKGROUND OF THE INVENTION

1. Field of the Invention

This invention relates generally to orthotic devices generally and particularly to spinal orthotic devices useful to support the spine to provide varying degrees of immobilization of portions of the torso or trunk of the wearer.

2. Description of the Related Art

A common method of alleviating pain and promoting healing after an injury or spinal surgery is to provide stabilization of the patient's trunk and provide support for the involved spinal structural tissues. This is accomplished using a back brace or spinal orthosis. The terms brace and orthosis are used interchangeably herein.

There are a variety of spinal orthosis presently available, each possessing features which achieve varying degrees of support functions regarding the spine or related soft tissues. Of those which are generally accepted as the most useful, each have one or more features related to comfort to the wearer, the ease of use, and cost which also vary in degree. In most instances, one or more of these features are compromised to enhance other features.

Generally, it is accepted that a custom-made spinal orthosis, which is literally formed from a cast of the torso of the intended wearer, is believed to provide the highest degree of stabilization and support. However, custom made devices of this type possess drawbacks related to comfort, expense and the lack of adjustability should the dimensions or other circumstances of the wearer change during the time period required to wear the custom made device.

Highly adjustable devices, which may include elastic components of support, are advantageous relative to fitting a wide size range of persons and may offer some cost advantages. However, many of these devices offer a lesser degree of stabilization and support than desired.

There is also a class or type of spinal brace devices which are known as custom-fit. Such devices include pre-manufactured components which allow for some degree of latitude for fitting a given torso size and configuration. These devices may include adjustable features to achieve a better fit for the individual wearer. However, many of such custom-fit spinal orthosis rely upon flexible, non-rigid portions to achieve a certain degree adjustability or of comfort which may compromise the desired degree of immobilization and support of the wearer's trunk. Others of the custom fit type tend to be relatively limited in adjustment upon fitting and therefore require a greater number of standardized pre-fabricated components in order to accommodate a reasonable percentage of sizes and torso configurations typically encountered in the patient population.

There is a need for an improved custom-fit spinal orthosis of the type described which provides a satisfactory degree of comfort, manufacturing economy, and ease of proper fitting to the wearer, while also providing anterior, posterior, lateral and rotary control of the trunk equivalent to or closely approaching the same degree of immobilization of spinal structures achievable using the custom-made type torso cast.

BRIEF SUMMARY OF THE INVENTION

The present invention relates to a spinal orthosis or back brace which is custom-fit to the individual wearer. The invention comprises a pair of rigid, or at least semi-rigid, arcuate side panels. The side panels, when mounted in opposing relationship, form a generally cylindrical configuration surrounding at least most of the torso of the wearer. Also included is a rigid or semi-rigid discrete posterior panel. The posterior panel is heat-deformable so as to be readily custom-fit to the lumbar curve of the wearer and is disposed under the side panels directly over a selected length of the wearer's spine.

A rear portion of the arcuate side panels extend in overlying relationship to the wearer's back and the posterior panel. The side and posterior panels include openings aligned with one another to receive a fastener to fix the side and posterior panels to one another. The openings allow lateral adjustment of the upper and lower portions of the side panels relative to one another which permits the orthosis to fit a wider range of different torso proportions within a given selected size range. This feature permits more economical volume manufacture of a smaller number of standardized components to efficiently and effectively meet custom-fit requirements accommodating a wide range of torso configurations.

It is therefore one aspect of the present invention to provide a spinal orthosis or brace which provides a high degree of stabilization and support for the targeted area of the spine.

It is another aspect of the present invention to provide an orthosis of the type described which is relatively easy to custom-fit to the selected wearer in an efficient and effective manner.

It is yet another aspect of the present invention to provide an orthosis of the type described which lends itself to economical manufacture of fewer standardized components to cover a wide range of body types and sizes and yet maintain the desired custom fit relationship with the individual wearer.

It is a further aspect of the present invention to provide a thoracic lumbar sacral orthosis (TLSO) or a lumbar sacral orthosis (LSO) which provides a high degree of comfort to the wearer which encourages patient usage of the device over the prescribed period of healing.

It is yet another aspect of the present invention to provide a TLSO or LSO which provides a rigid or semi-rigid shell-like configuration surrounding substantially the entire circumference of the wearer's torso to provide anterior, posterior, lateral and rotary control. This provides more positive stabilization of the wearer's trunk to promote the desired post-surgical or post-injury healing.

Other aspects and objects of the present invention will become apparent from the following description.

BRIEF DESCRIPTION OF THE SEVERAL VIEWS OF THE DRAWINGS

FIG. 16 is a bottom view of the male member portion of a preferred fastener forming a part of a preferred embodiment of the present invention;

FIG. 17 is a side elevational view of the male member shown in FIG. 16;

FIG. 18 is a bottom view of the female portion of a preferred fastener forming a part of a preferred embodiment of the present invention; and FIG. 19 is a side elevational view of the female portion shown in FIG. 18, the internal threaded bore being shown in section for clarity of illustration.

Figure 1:
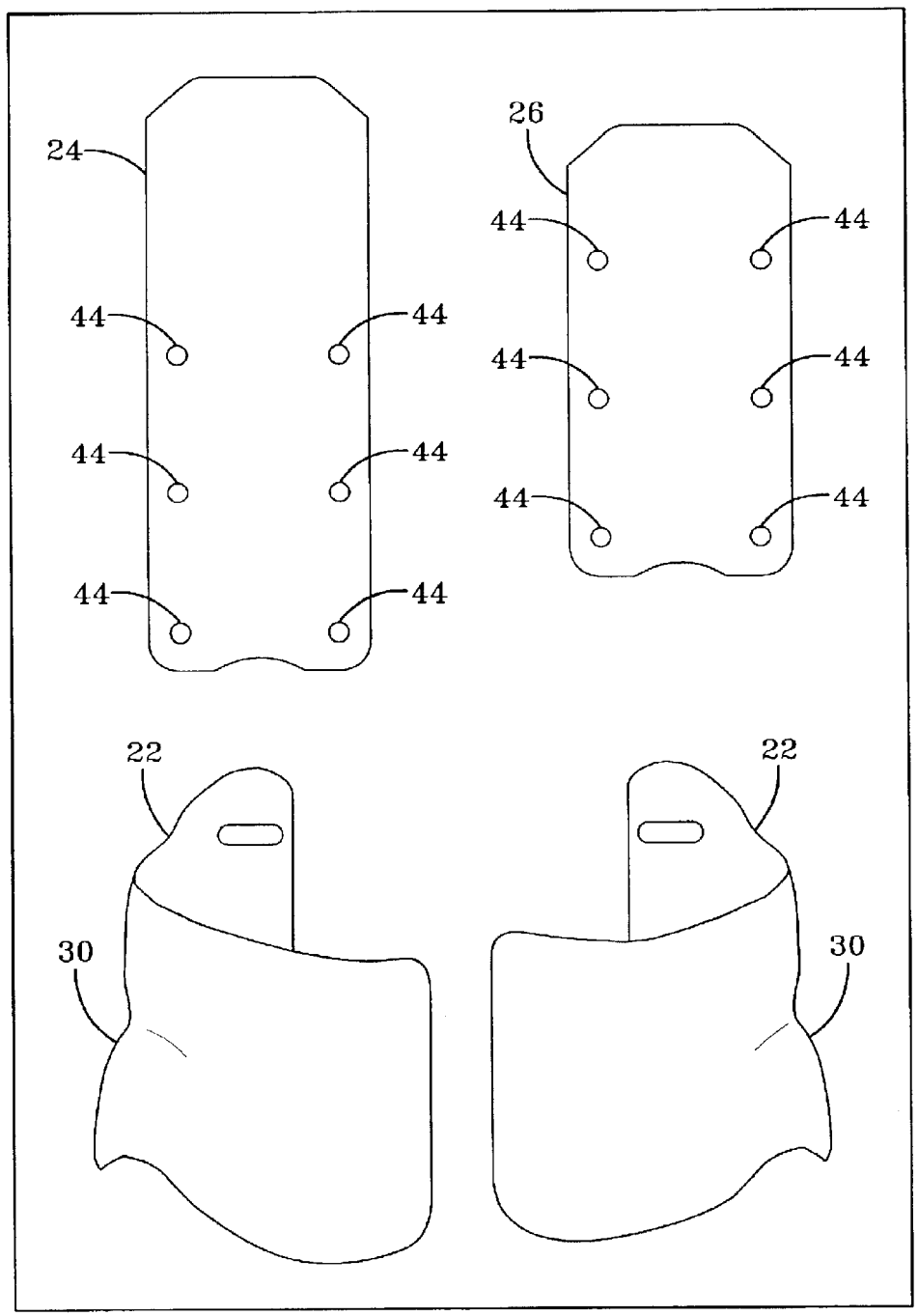
FIG. 1 is a perspective view showing individual components of an LSO spinal orthosis forming part of the present invention in exploded relationship.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or term similar thereto are often used. They are not limited to direct connection, but include connection through other elements where such connection is recognized as being equivalent by those skilled in the art. In addition, components are illustrated which are of a type which perform well known functions. Those skilled in the art will recognize that there are many, and in the future may be additional, alternative arrangements which are recognized as equivalent because they provide the same function for the same purpose operations on the signals.

DETAILED DESCRIPTION OF THE INVENTION

Figure 3:
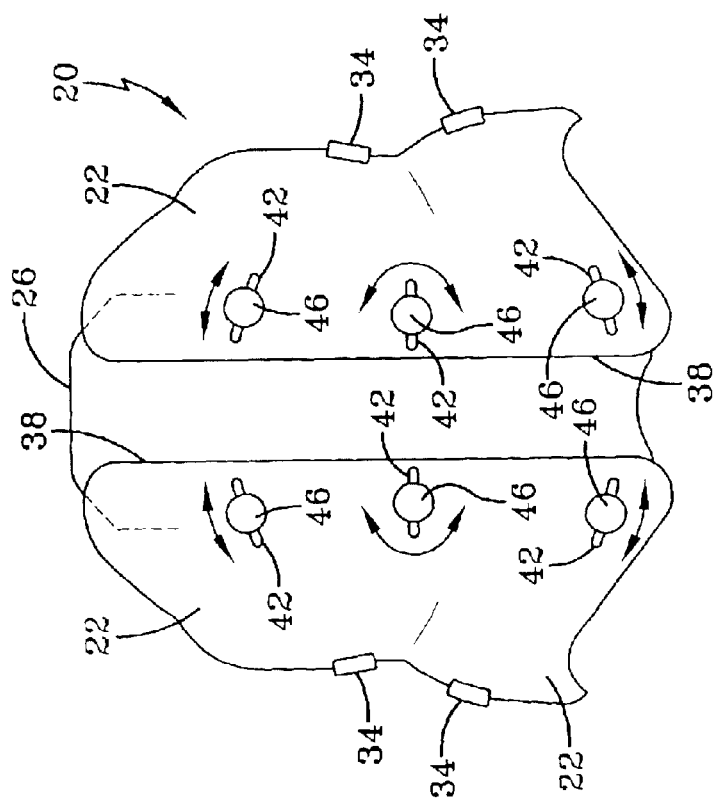
FIG. 3 is a rear elevational view illustration of the embodiment shown in FIG. 1 without showing the image of the torso of the wearer.
Figure 2:
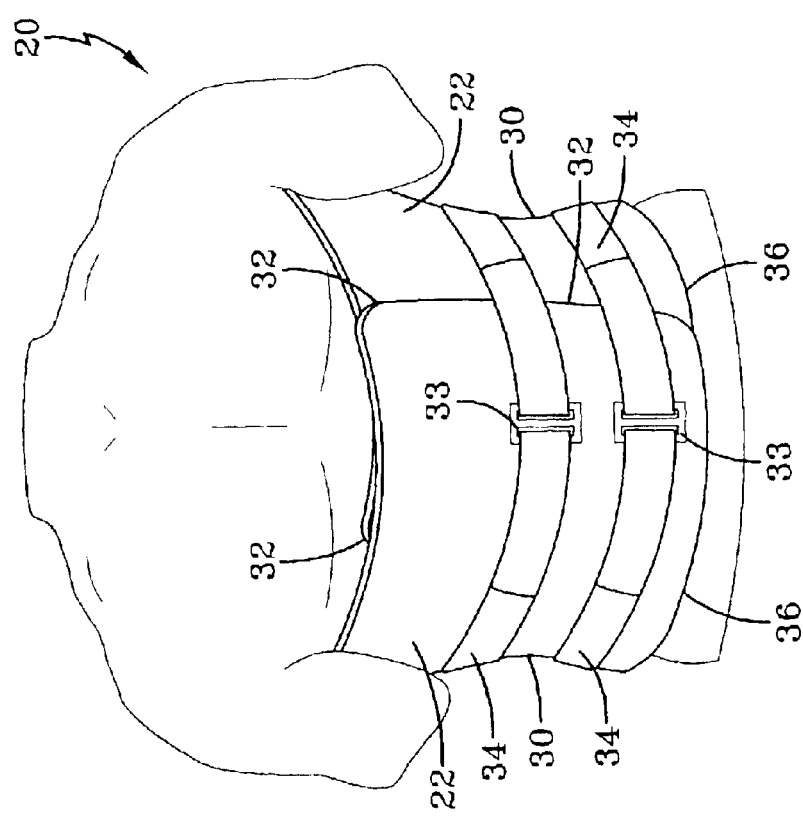
FIG. 2 is a front elevational view illustrating an embodiment of the present invention in its intended operative position upon the torso of a wearer.

A spinal brace or orthosis, indicated generally at 20, constructed in accordance with the present invention, is illustrated in FIGS. 1–3 and includes a pair of arcuate side panels 22 and one discrete posterior panel 24 or 26. The only difference between posterior panels 24 and 26 is the height dimension which is selected depending upon whether the orthosis 20 is designed to support only the lumbar sacral region, referred to by those in the art as an LSO type, or the thoracic lumbar sacral region, referred to as a TLSO. Otherwise, for purposes of the present invention, panels 24 and 26 are equivalent.

Side panels 22 and posterior panel 24 or 26 are preferably constructed from a heat-deformable or moldable semi-rigid or rigid material, preferably a suitable plastic. The terms semi-rigid or rigid, as used herein, mean that the panels may have some degree of flexibility, yet comprise an inelastic material having sufficient rigidity to provide a high degree of trunk immobilization when the components of orthosis 20 are operatively mounted on a wearer as described herein.

Side panels 22 are configured to conform to the torso of the wearer, such as seen in FIG. 2 when mounted on the wearer. The frontal portions of panels 22 surround the abdominal area from below the wearer's arm pits to the pelvic area. The front portion of an LSO brace should not extend lower than the pubic symphysis or higher than the xiphoid process just below the sternum. The rear portions of panels 22 extend between the lower end of the scapula over the back of the wearer to near the sacrococcygeal joint for an LSO design. In the LSO design, posterior panel 26 extends over the spine area generally about the same vertical length as the panels 22. For a TLSO design, the posterior panel 24 will extend up to the spine of the scapula and the front portions of panels 22 may also extend higher, if desired, to the upper end of the sternum.

Preferably panels 22 cover a portion of the upper hip area of the wearer. Each side panel 22 preferably includes a convex curve portion 30 adapted to accommodate the transition area on each side of the torso between the wearer's waist and hip.

For any given standardized size range, such as small, medium or large for example, frontal edges 32 of each panel 22 are adapted to overlap a portion of the opposing panel 22 so as to provide a closed configuration over the abdominal area of the wearer.

One or more pairs of flexible straps, such as 34, may be employed to function as a means to pull side panels 22 toward one another and into a releasably fastened, close fit relationship with the wearer's torso.

One end of strap 34 may be fixed to one of the panels 22 with its free end aligned to extend horizontally across to the opposing panel 22. One preferred form of fixing strap 34 to the opposing panel 22 may take the form of the well-known Velcro hook and loop type fastener strips on the outward facing surface of the opposing panel 22 and the inwardly facing surface of the extendable strap 34. However, other forms of equivalent connecting means may also be used to advantage, including, for example, snaps, buckles, clasps and the like.

Using one form of the hook and loop fastening construction as seen in FIG. 2, each free end of an opposing flexible strap 34 extends laterally across toward the opposing panel 22. The outer surface of each strap 34 includes a cooperating strip of the hook and loop type. A conventional double buckle 33 accepts the free end of each strap 34. Then each strap 34 may be doubled over itself and fastened via the hook and loop structure upon itself to draw side panels 22 toward one another to the desired degree. One or more pairs of additional straps 34 may be similarly employed as deemed desirable to accomplish the intended purpose as described herein.

It should be noted that the lower anterior edge 36 of each panel 22 is preferably disposed near the upper end of the pubic synthesis to assure coverage of most of the abdominal area of the wearer. When properly closely fitted on the wearer in accordance with the present invention and fixing of straps 34, the brace 22 provides a desirable increase in internal abdominal pressure. This increase in internal pressure in the abdominal cavity provides additional support to the spinal structures and the soft tissues supporting the spine.

Figure 5:
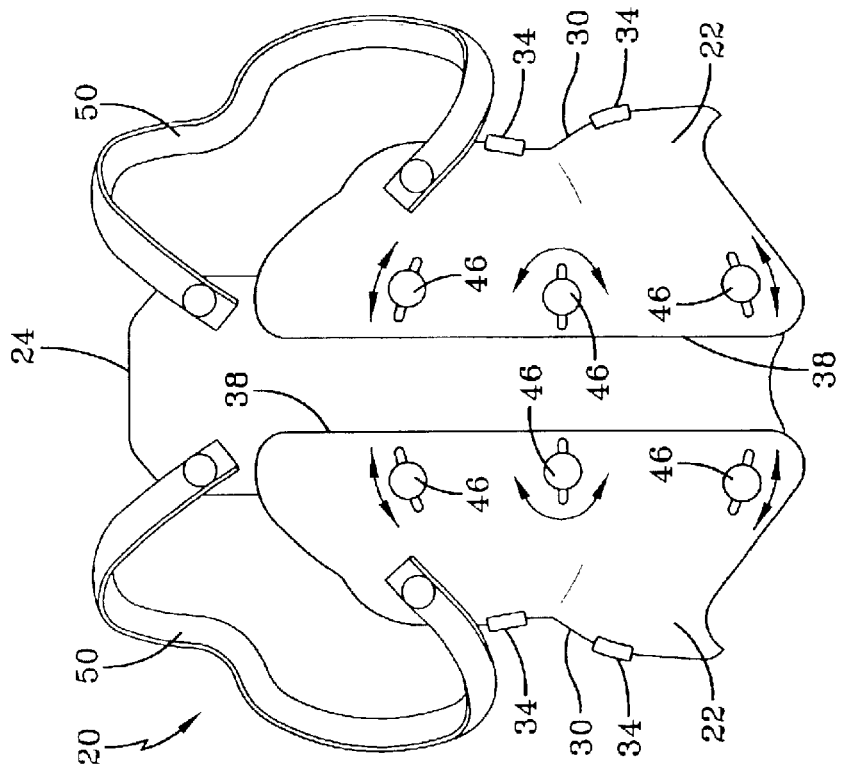
FIG. 5 is a rear elevational view similar to FIG. 3 showing the embodiment of the present invention illustrated in FIG. 4.

Each arcuate side panel 22 includes a rear portion extending across the back of the wearer's torso and may terminate in opposing posterior edges 38 located near the spinal area of the wearer, as shown in the embodiments seen in FIGS. 3 and 5.

The discrete posterior panel 24 or 26 is disposed under the rear portions of each side panel 22 over the wearer's back and aligned with the wearer's spine.

Panels 24 or 26 are preferably made of a semi-rigid or rigid, heat deformable plastic material. This allows essentially a pre-fabricated strip of planar material having preselected dimensions, to be heated and bent into a longitudinally curved configuration closely conforming to the measured anatomical curve of the lumbar vertebrae of the wearer. For convenience, the pre-fabricated strips may include a 25 degree curvature in the lumbar area which is typically within plus or minus a few degrees of the lumbar curve in most patients. Any final bending and molding to custom fit the posterior panel to the individual patient's lumbar curve would involve a modification typically less than three or four degrees.

Many plastic materials suitable for posterior panels 24 or 26 and side panels 22 are well-known to those skilled in the art. For posterior panels 22, those which soften sufficiently to allow relatively easy bending and molding into the required curved shape upon moderate heating and regain the original rigidity upon subsequent cooling are preferred. One preferred material is a polypropylene having a thickness in the preferred range of about 0.1 to 0.15 inches, and more preferably between about 0.12 to 0.13 inches. This range of thickness provides a panel of ample rigidity after being bent or molded into the final curved shape, is relatively inexpensive and is relatively lightweight for the comfort of the wearer.

The preferred thickness for side panels 22 is in the range of about 0.4 to 0.7 inches dependent upon the type of plastic material used. The choice of plastic material should take into account strength, hardness, and of course cost. Using an acrylonitrite, butadiene, styrene plastic composition, commonly referred to as ABS, it has been found that a thickness of about 0.6 inches performs well to provide the rigid arcuate configuration desired and suitably meet the other desired characteristics mentioned above. However, other materials in a range of thicknesses can be used to accomplish the desired results without departing from the present invention.

After heating and forming the posterior panel into the desired curved configuration fitting the patient's lumbar curve, cooling the panel to ambient temperature returns the panel 24 or 26 to its original semi-rigid or rigid condition. When positioned as described herein, the curved posterior panel closely fits over the spinal area of the wearer to provide, in combination with side panels 22, the stabilizing support intended when the brace 20 is appropriately fitted and fastened upon the wearer.

A plurality of vertically spaced slots, such as at 42, are provided adjacent to posterior edges 38 of each panel 22. Each slot 42 of one panel 22 is aligned in opposing, laterally spaced relationship to a similar slot 42 in the opposing panel 22 as seen in FIGS. 3 and 5.

In a cooperative manner, panels 24 and 26 are provided with vertically spaced openings 44 shown in the form of circular holes. Opposing ones of such holes 44 in a respective panel 24 or 26 are disposed for alignment with horizontally extending slots 42 in panels 22 when panel 24 or 26 is disposed beneath the rear portion of panels 22. Preferably, a threaded fastener, such as at 46, provided with a relatively large washer or an equivalent structure may be usefully employed to fix panel 24 or 26 to side panels 20 so as to more widely disperse the force or pressure applied by the fastener against the user's back.

A preferred fastener 46 of the Chicago type, shown in detail in FIGS. 16–19, includes a male threaded post 47 provided with an enlarged head 49. Post 47 mates within a tubular post 51, provided with internal female threads which is integrally formed with an enlarged back plate 53.

The enlarged head 49 and back plate 53 tend to disperse the pressure or force applied to the wearer's back when fastener 46 extends through holes 44 and slots 42 and is tightened to snugly fix the posterior and side panels to one another. The inner facing surfaces 55 and 57 may include an irregular or a roughened pattern to increase frictional engagement with the underlying surfaces of the panels upon final tightening of the fastener.

It should be pointed out the position of fasteners 46 within slots 42 determine the relative position of panels 22 to one another. Moving panels 22 proportionately toward or away from one another expands or contracts the generally cylindrical volume encompassed by brace 20. Movement of the upper or lower portions of each panel toward or away from the opposing panel provide for adjusting the interior volume of the upper and lower torso portions relative to a selected size and configuration standard. Therefore, persons having a larger or smaller upper torso configuration relative to their lower torso, compared to a selected average torso configuration, may be more readily accommodated to the desired custom fit within a given standardized size range.

This feature is important to provide an improved custom-fit device, yet minimize the number of standardized size ranges of pre-fabricated side panels 22 necessary to service the largest percentage of potential wearers. It should be noted that such an adjustment feature is accomplished using rigid or semi-rigid components which ultimately form a substantially rigid, close-fit cylindrical configuration surrounding the wearer's torso. This substantially rigid configuration provides a degree of stabilization and trunk support substantially equivalent to that achievable with a custom-made orthosis.

Figure 4:
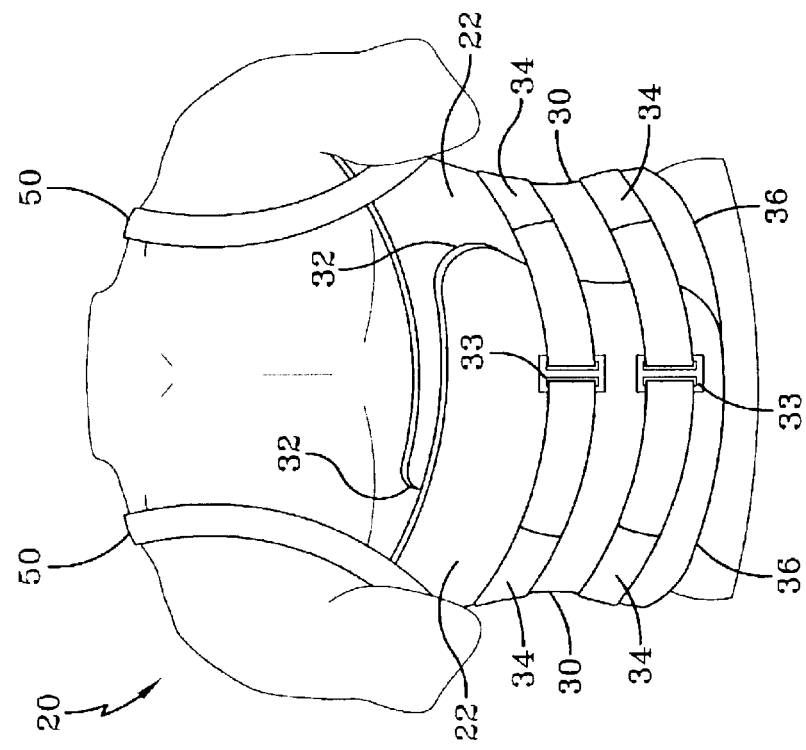
FIG. 4 is a front elevational view similar to FIG. 2 illustrating another embodiment of the present invention.

With specific reference to FIGS. 4 and 5, the TLSO embodiment of the present invention using posterior panel 24 is shown which provides thoracic as well as lumbar sacral support. The difference between the embodiment shown in FIGS. 2 and 3 and that shown in FIGS. 4 and 5 relate only to the use of the longer posterior panel 24 instead of the shorter panel 26 and the provision of a pair of inelastic, flexible shoulder straps 50. Straps 50 extend over the shoulders and under the arm pits of the wearer to cooperate with the other components of brace 20 to reduce the mobility of the upper spinal column of the wearer. Each shoulder strap 50 is fixed at one end to panel 24 and at the opposing end to a respective one of side panels 22 as seen in FIGS. 4 and 5. The length of straps 50 may be made adjustable to fit snugly to the wearer in any suitable well-known and conventional manner as will be understood by one of ordinary skill. Upon tightening straps 50, the upper portion of brace 20 is stiffened to provide the intended support to the thoracic area and related spinal structures.

The remaining components of the embodiment shown in FIGS. 4 and 5 are the same as in the earlier described embodiment and carry the same reference numerals as the corresponding components shown in FIGS. 2 and 3.

Figure 7:
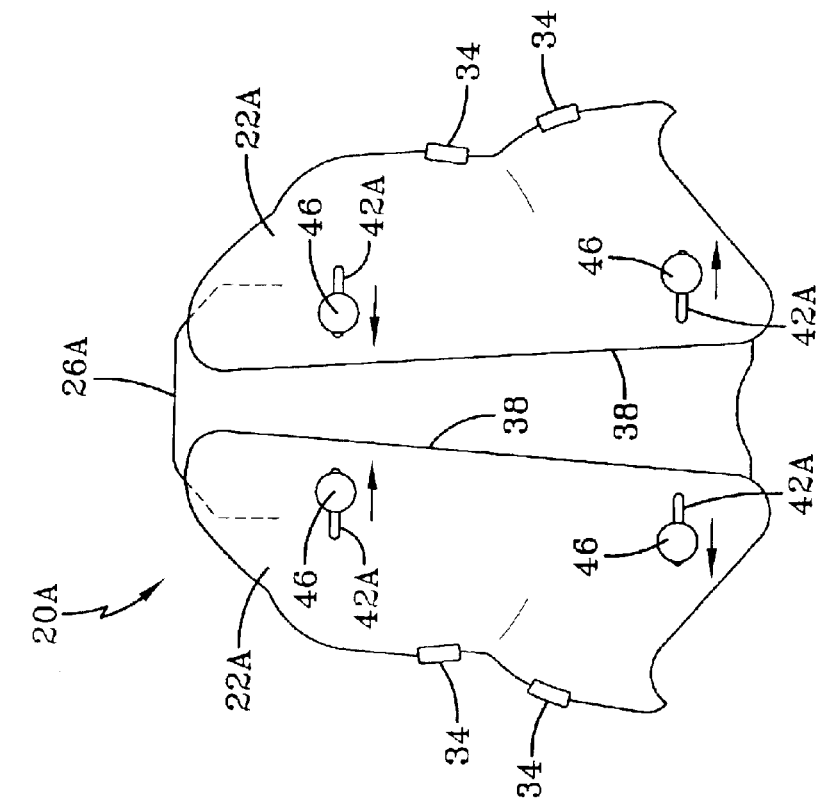
FIG. 7 is a rear elevational view similar to the view shown in FIG. 6 illustrating adjusting the rear panels relative to one another in a lateral direction opposite to that shown in FIG. 6.
Figure 6:
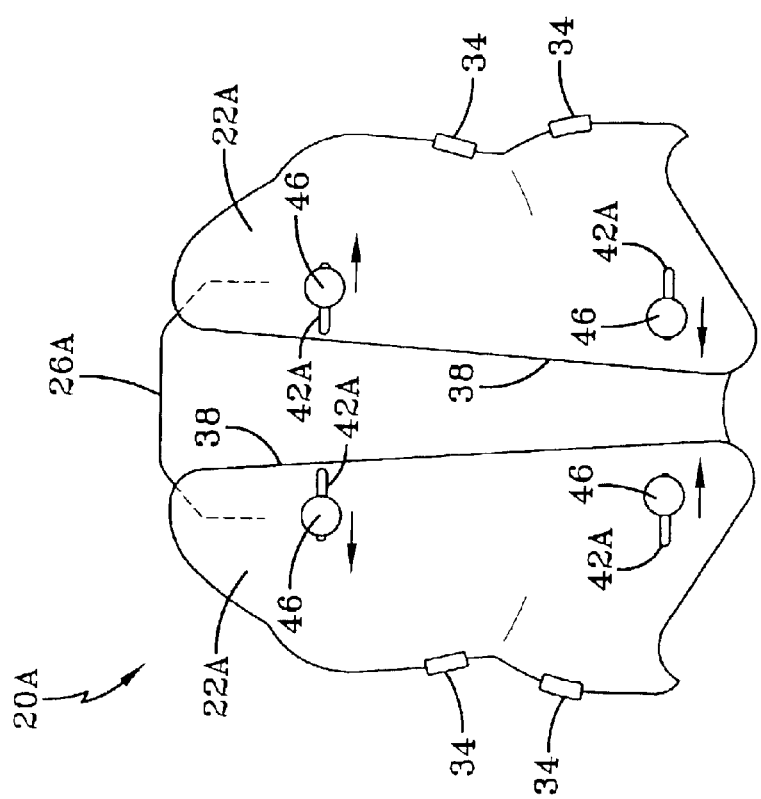
FIG. 6 is a rear elevational view of another embodiment of the present invention illustrating an modified posterior fastening arrangement for connecting the arcuate side panels to the posterior panel compared to that shown in FIGS. 3 and 5.
Figure 8:
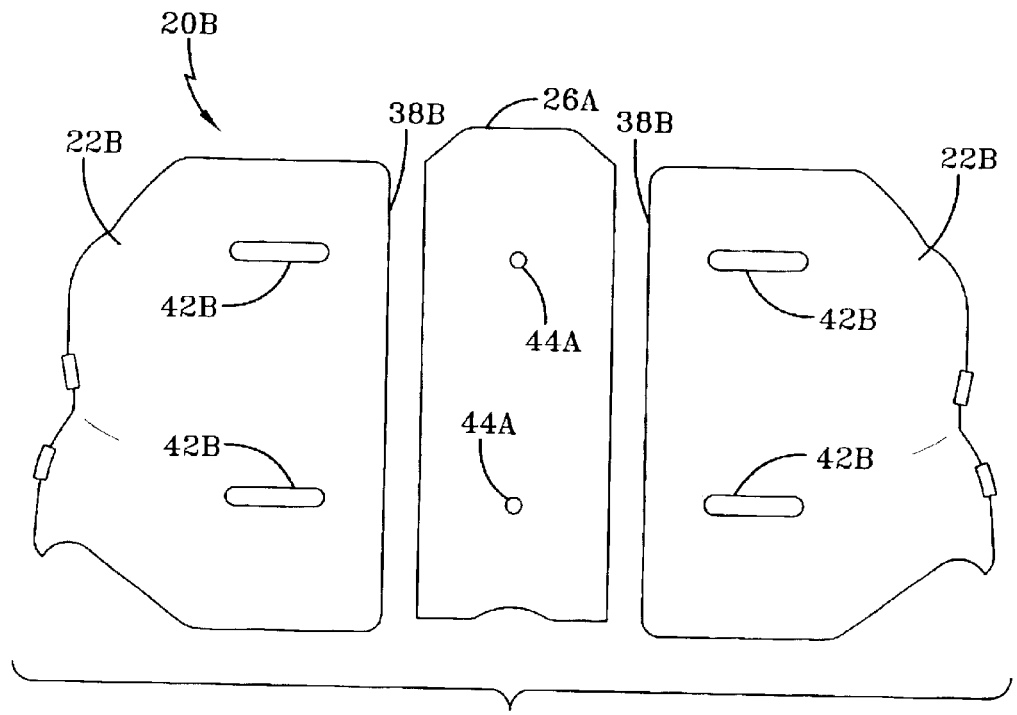
FIG. 8 is a rear elevational view of another embodiment of the present invention showing another modified arrangement for connecting the side panels to the posterior panel illustrating the components ion exploded relationship to one another.

Another preferred embodiment of the present invention is shown in FIGS. 6 and 7 which differs from the earlier described embodiments relative to the number of slots and holes provided in the posterior panel 24-A and the side panels 22-A. As seen in FIGS. 6 and 7, only two pairs of slots 42-A and aligned holes 44-A are required in posterior panel 26-A to accomplish the equivalent function as previously described regarding slots 42 and holes 44.

As shown in FIGS. 6 and 7, upon positioning of fasteners 46 at selected positions along slots 42-A while maintaining a selected fixed position of holes 44-A in posterior panel 24-A, the position of the upper portion of each panel 22-A relative to its lower portion may be adjusted to expand or contract the relative interior volume of the upper and lower portions of side panels 22-A. In a similar manner as previously described, this adjustment feature accommodates an improved close fit to particular anatomical contours of a wearer's torso, which deviate from a selected standard contour.

As best illustrated in FIGS. 6 and 7, it is evident that the posterior edges 38 of opposing panels 22-A can be tilted toward and away from one another to modify the proportional relationship between the upper torso area and the lower torso area engaged by brace 20. Within a selected size range, a given anatomical proportional contour of the torso may be selected as an average and used as a standard. Based upon such a standard, the dimensions and contour of the side panels 22-A may be selected such that the fixed positioning of fasteners 46 at approximately the midpoint of slots 42 or 42-A in the described embodiments would define the selected standard torso configuration relative to the proportions of the upper and lower trunk area of a wearer. This standard may be adjusted, as described, by positioning the fasteners 42 or 42-A toward either end of slot 42 or 42-A. This accommodates variations from the selected standard for a greater percentage of torso types otherwise generally within a selected size range.

In a similar manner, posterior panels 24, 24-A and 26, 26-A may be prefabricated using a set of standardized lengths to accommodate any significant difference in the length dimension necessary to extend over the necessary portion of the wearer's spine to provide the intended immobilization and support of the wearer's trunk. Typically, however, it has been found there is not a great difference in length necessary to accommodate differences in the height of most persons for the LSO or TLSO type brace.

It should also be noted that the spinal orthosis of the present invention may include a conventional interior lining comprising a pad of resilient material, preferably a foamed plastic, not shown. The pad provides an additional degree of comfort to the wearer. Such a pad lining preferably may be releasably fixed to the interior walls of panels 22 in any conventional manner well-known to those of ordinary skill in the art. A separate pad liner may also be releasably fixed to the inner facing surface of posterior panels 24 or 26.

Now referring to FIGS. 8–11, another preferred embodiment of the present invention is illustrated. The basic difference between the embodiment shown in FIGS. 8–11 relative to that shown in FIGS. 6 and 7 is that the posterior edges 38-B of panels 22-B are extended such that the edges 38-B overlap portions of the opposing side panel 22-B. Modified components or parts of this embodiment relative to the corresponding embodiments shown in the preceding FIGS. are indicated by the same reference numeral followed by the letter "B".

One primary advantage of having overlapping posterior edges 38-B is that the number of slots 42-B, holes 44-B and fasteners 46-B may be reduced and yet provide an equivalent connecting function compared to those previously described in relation to the other embodiments. This overlapping feature of the rear portion of panel 22 is advantageous as it tends to simplify and reduce the time necessary for the custom-fitting procedure as compared to the embodiments shown in the preceding Figures.

Figure 9:
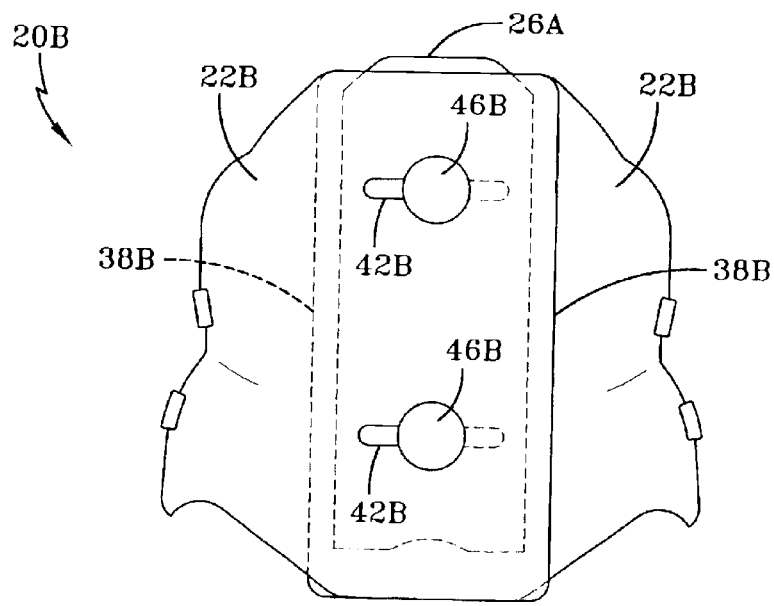
FIG. 9 is a rear elevational view of the embodiment shown in FIG. 8 illustrating the component panels connected to one another as if they were mounted on a wearer.

As best seen in FIG. 9, the spinal brace 20-B is shown in assembled form with the opposing edges 38-B of the side panel 22-B on the left, overlying a portion of the side panel 22-B seen on the right. The embodiment shown in FIGS. 8–11 tends to permit the practical length of slots 42-B to be increased compared to the earlier described embodiments without sacrificing structural integrity or fit. The greater the length of slot 42-B, the greater degree of adjustability may be attained.

It should also be noted that the disposition of slots corresponding to 42 and openings or holes corresponding to 44 may also be reversed between the panels 22 and posterior panels 24 or 26 without departing from the present invention. However, placing the slots in the side panels and the holes in the posterior panel as shown is believed to be more preferred.

The custom-fitting of brace 20 to the wearer should be done by properly trained personnel and is essentially the same for all embodiments. Side panels 22 are held in surrounding relationship to the torso and slots 42 are aligned with the openings 44 in the underlying posterior panel 26 or 24.

Referring specifically to the embodiment shown in FIGS. 8–11, the fitting may be more quickly accomplished since only two fasteners 46-B are required. As seen in FIG. 9, the opposing posterior edges 38-B are aligned substantially parallel to one another and fasteners 46-B are disposed through approximately the middle of slots 42-B and into the underlying opening 44 in posterior panel 24-B and tightened lightly to connect the rear portions of panels 22-B to the posterior panel.

Figure 11:
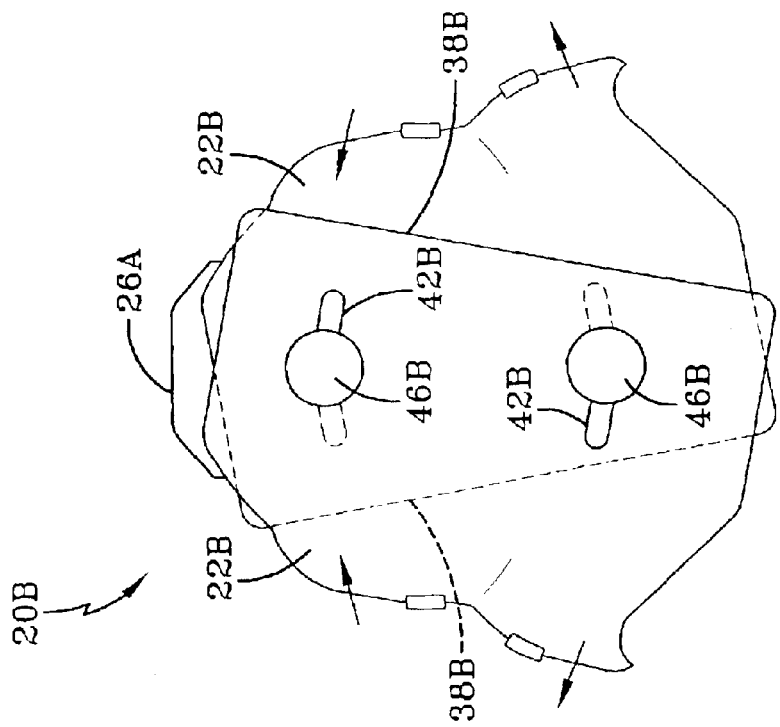
FIG. 11 is a rear elevational view of the embodiment shown in FIG. 9 illustrating the side panels laterally adjusted in an opposite position relative to that shown in FIG. 10.
Figure 10:
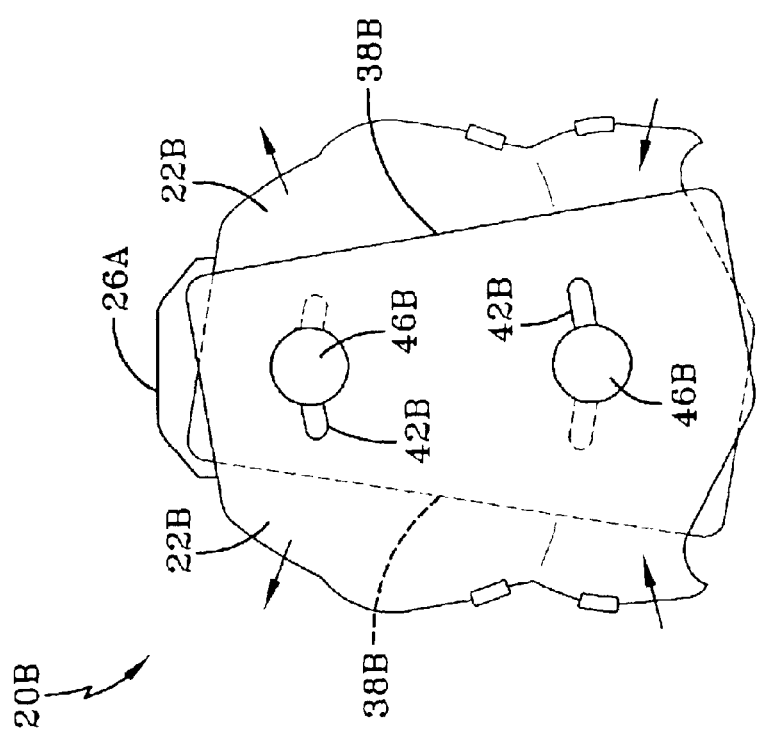
FIG. 10 is a rear elevational view similar to FIG. 9 illustrating the side panels laterally displaced compared to that illustrated in FIG. 9 to adjust the fit to a given wearer's torso proportions.
Figure 12:
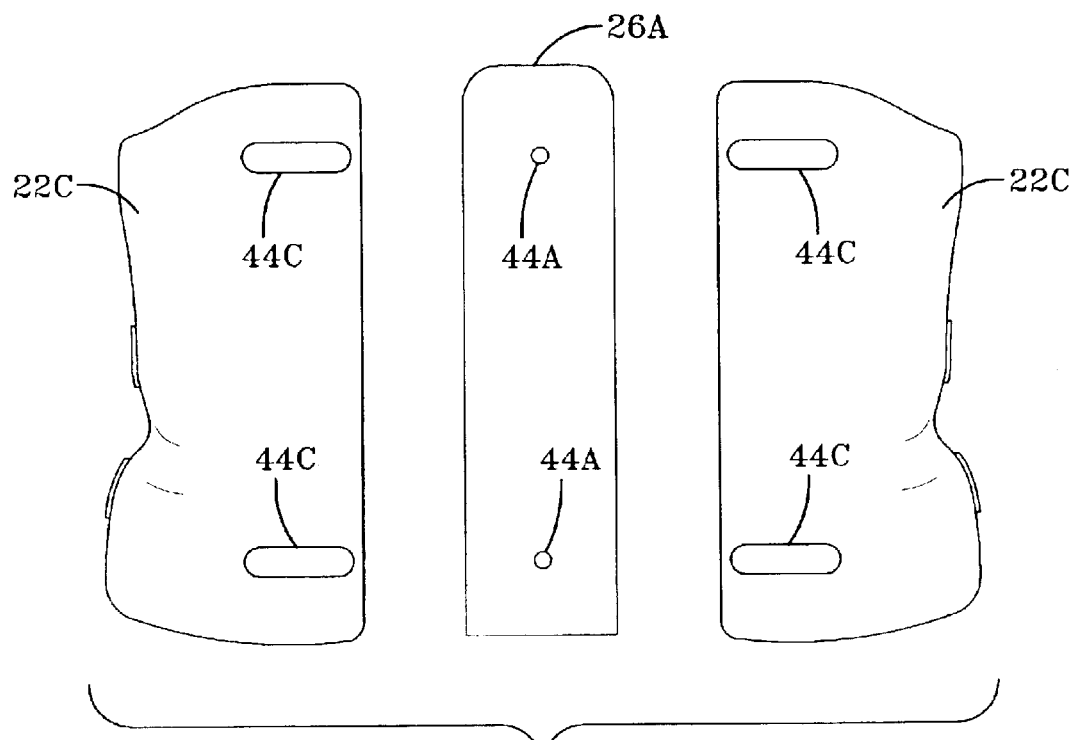
FIG. 12 is a rear elevational view of another embodiment of the present invention illustrating the components of a TLSO version of the orthosis in an exploded relationship.
Figure 13:
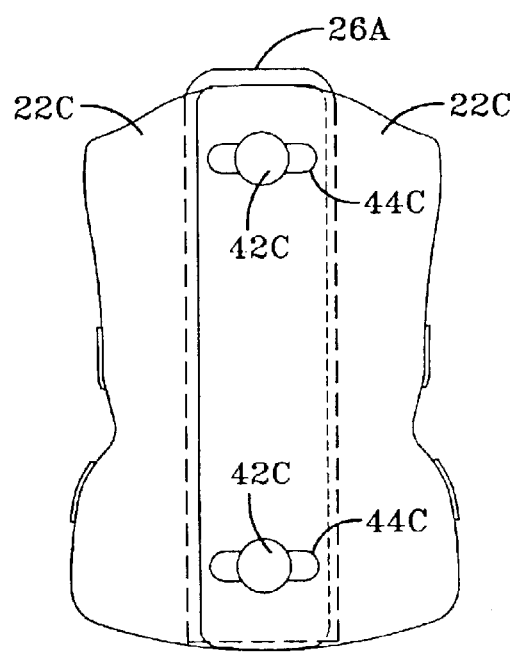
FIG. 13 is a rear elevational view of the embodiment shown in FIG. 12 illustrating the components panels connected to one another as if they were mounted on a wearer.
Figure 15:
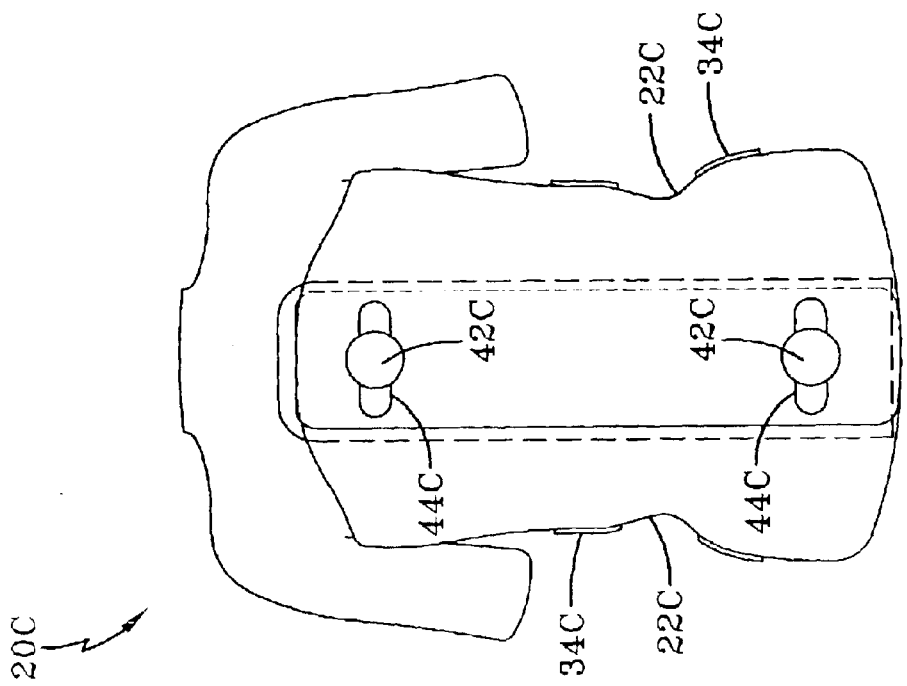
FIG. 15 is a rear elevational view of the embodiment shown in FIG. 13 illustrating the embodiment mounted on a wearer's torso.
Figure 14:
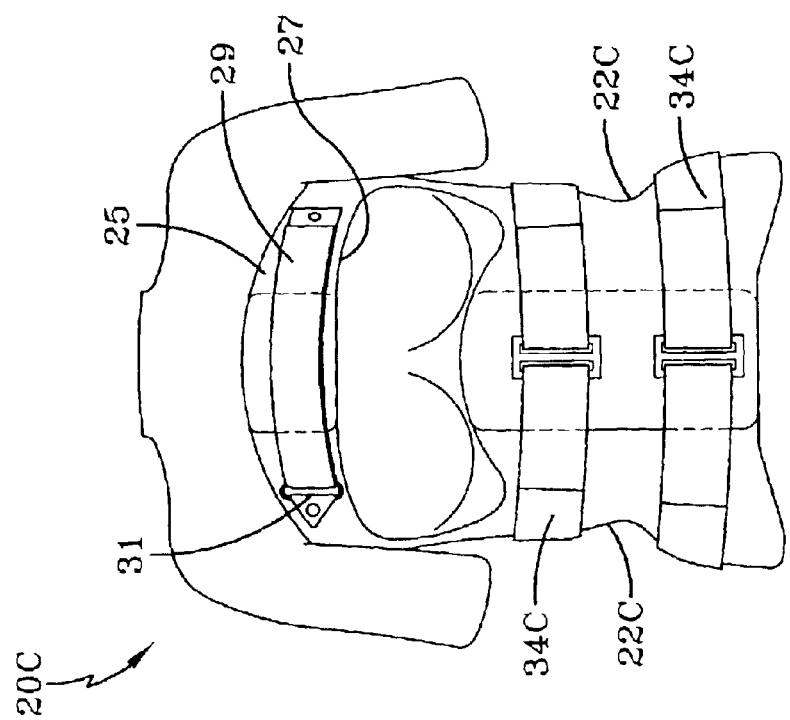
FIG. 14 is a front elevational view of the embodiment shown in FIG. 13 illustrating the embodiment mounted on a wearer's torso.

FIGS. 10 and 11 illustrate the maximum adjustment in opposing directions employing the construction of the present invention relative to accommodating persons having larger or smaller upper and lower torso proportions relative to the proportions of a selected standard configuration which is represented by the arrangement shown in FIG. 9. As seen in FIG. 9, posterior edges 38 are aligned substantially parallel to one another.

As seen in FIG. 10, the circumference of the lower torso portion of the brace 20-B is reduced relative to the upper portion to accommodate a corresponding torso configuration of a wearer. This may be accomplished by moving the upper portion of side panels 22-B away from one another prior to final tightening of fasteners 46-B within slots 42-B and openings 44-B. This has the effect of pivoting the side panels about the holes 44-A in the posterior panel 26-A. In making this adjustment, the fasteners 44-B are disposed toward opposite ends of the upper and lower slots 42-B. Upon tightening fasteners 46-B in the conventional manner, the brace is releasably fixed in this modified disposition.

Adjustment of the lower portion of brace 20-B is accomplished in the reverse manner, as shown in FIG. 11, to expand the circumference of the lower torso portion of brace 20-B relative to that shown in FIGS. 9 and 10. This has the effect of reducing the circumference of the upper portion of the brace 20 covering the upper torso.

Of course, the side panels 22-B may also be equally moved toward and away from one another to dispose fasteners 46-B at the left or right end of upper and lower slots 42-B. In this manner, the general contour shown in FIG. 9 is maintained, however, the circumference of the upper and lower portions of brace 24 has been expanded or contracted equally to accommodate the torso of the wearer.

The fasteners 46 in any of the embodiments are typically positioned as described and initially tightened lightly to connect panels 22 together in the rear and may be subsequently tightened once the intended fitting adjustments have been made.

Next, the frontal edges 32 of panels 22 are urged together and strap 34 is fastened to strip 35 to hold the brace 20 in a general initially mounted position. The trained personnel then begin to make any further adjustments in the positioning of fasteners 46 deemed needed and adjust the strap or straps 34 accordingly until a proper fit is accomplished. Simply loosening the head of a fastener 46 allows further adjustment, followed by tightening the fastener until the desired fit and comfort level has been achieved.

Now referring to FIGS. 12–16, another embodiment of the present invention is shown. Components of this embodiment are identified by the same reference numeral used for a corresponding component followed by the letter "C". The primary difference of the embodiment of FIGS. 12–15 relates to a modification of the frontal portion of the side panels to include an upper portion located above the breast line of the wearer. This construction provides a TLSO orthosis which does not require the straps 50 such as shown in the embodiment illustrated in FIGS. 4 and 5.

Referring to FIGS. 12–15, side panels 22-C include slots 44-C and extend over the spine of a wearer to a height greater than the LSO version shown in the preceding Figures such as FIG. 3. Additionally, the panels 22-C include an upper portion 25 which overlaps the corresponding portion 25 of the opposing panel and extends across the wearer's chest above a cut-out portion 27 aligned with the breast of the wearer. An additional strap 29 is fixedly provided on one panel 22-C which, in cooperation with a buckle 31 fixed on the opposing panel and velcro-like strips, function to tighten and hold the upper portion of panels 22-C in close-fitting relationship in a similar fashion to straps 34-C which draw the lower torso portion of brace 20-C together.

The added upper portion 25 of each side panel 22-C function to inhibit forward bending in the thoracic spine. Upon properly mounting brace 20-C, upper portion 25 is effectively connected to posterior panel 26-A as well as being an integral part of each side panel 22-C. This construction is preferred and replaces the need and function of straps 50 shown in FIG. 5.

The rearward facing portions of side panels 22-C are the same in all essential respects to the embodiment shown in FIGS. 12–15 regarding slots 44-C, fasteners 46-C and TLSO type posterior panel 26-A as previously described herein. This includes adjusting the relative proportions of the upper and lower torso portions comprising brace 20-C relative to a selected standard as described herein. The description of such adjustments being essentially identical to those described for the embodiment of FIGS. 12–15 will not be repeated since it is believed unnecessary for one of ordinary skill in the art to understand how to make and use the present invention and this embodiment.

In view of the foregoing description, it should be readily understood that the present invention provides a custom-fit type of LSO and TLSO type orthosis wherein prefabricated components may be manufactured in an economical manner to provide a degree of immobilization of the trunk of the wearer equal to or closely approaching the results obtained using a custom-made brace.

Further, a custom-fit LSO or TLSO constructed in accordance with the present invention provides a degree of comfort which tends to increase patient compliance for the prescribed time period during which the brace should be worn. The present invention also provides prefabricated components which may be readily custom-fit to the wearer in a relatively facile and quick manner compared to prior custom made spinal braces and yet provide a closely similar level of stabilization and spinal support more economically.

While certain preferred embodiments of the present invention have been disclosed in detail, it is to be understood that various modifications may be adopted without departing from the spirit of the invention or scope of the following claims.

What is claimed is:

1. A spinal orthosis comprising, in combination;
   a) a pair of at least semi-rigid, arcuate side panels configured to fit opposing one another in close-fitting relationship around a wearer's torso, each of said side panels having an anterior edge disposed in overlapping releasably fixed relationship to the anterior edge of the opposing side panel to cover a major portion of the front of a wearer's torso, a posterior edge disposed near the spinal column of the wearer, and at least a vertically spaced pair of horizontally extending slots having a selected length and disposed near, but spaced from the posterior edge;
   b) a discrete, at least semi-rigid posterior panel disposed beneath a portion of each of said side panels and including a plurality of vertically spaced openings aligned to mate with the horizontally extending slots formed in each of said side panels, said posterior panel having a length including a longitudinal curve selected to conform to the lumbar curve of the wearer;
   c) at least two fasteners, a respective one extended through one of said horizontal slots in said side panels and an aligned opening in said posterior panel to fix said side panels to said posterior panel.

2. The spinal orthosis defined in claim 1 further including one or more flexible straps having one end fixed to one side panel and a free end disposed to extend over the overlapping anterior edges of said side panels and releasably connected to the opposing side panel for urging said side panels toward one another into said close fitting relationship with the wearer's torso.

3. The spinal brace defined in claim 1 wherein said posterior panel comprises a heat deformable material which can be selectively configured upon heating to substantially conform to the wearer's lumbar curve.

4. The spinal orthosis defined in claim 1 wherein the posterior edges of said side panels extend in overlapping relationship to one another.

5. The spinal orthosis defined in claim 4 wherein horizontally extending slots in each of said side panels are aligned to overlap with a horizontal slot in the opposing side panel, and a single fastener may be extended through a respective one of said overlapping slots and one of said openings in said posterior panel to fix said side panels and said posterior panel to one another.

6. The spinal orthosis defined in claim 1 wherein the configuration of said side panels defines an interior space related to a selected configuration of a human's torso and wherein said interior space may be modified by moving the fixed position of a respective one of said fasteners within the confines of a respective one of said slots.

* * * * *